United States Patent
Bentley et al.

(10) Patent No.: US 6,409,131 B1
(45) Date of Patent: Jun. 25, 2002

(54) EASILY RE-POSITIONABLE, QUICK ATTACH AND REMOVE, MULTIPLE PURPOSE SUPPORT SYSTEM

(76) Inventors: Ronald L. Bentley, 1428 Bartlett Ave., Altoona, WI (US) 54720; Bruce R. Rosenau, 4400 LaSalle St., #12, Eau Claire, WI (US) 54703

(*) Notice: Subject to any disclaimer, the term of this patent is extended or adjusted under 35 U.S.C. 154(b) by 0 days.

(21) Appl. No.: 08/801,043

(22) Filed: Feb. 14, 1997

(51) Int. Cl.⁷ ................................................ A47B 6/06
(52) U.S. Cl. ........................ 248/219.4; 248/230.1; 248/230.7
(58) Field of Search .................... 248/219.4, 218.4, 248/219.1, 220.1, 230.1, 230.2, 230.7, 230.8, 231.21, 231.81, 229.16, 229.26, 228.7; 5/503.1

(56) References Cited

U.S. PATENT DOCUMENTS

| | | | |
|---|---|---|---|
| 1,105,083 A | 7/1914 | Lamb | 248/229.16 |
| 1,410,798 A | 3/1922 | Cowdery | 248/517 |
| 1,951,930 A | 3/1934 | Harris | 294/5.5 |
| 2,036,655 A | 4/1936 | Storaasli | 248/229.13 |
| 2,216,886 A | 10/1940 | Langelier | 248/311.2 |
| 2,429,029 A | 10/1947 | Newbern | 248/218.4 |
| 2,443,762 A | 6/1948 | Boal | 248/538 |
| 2,487,094 A | 11/1949 | Brown | 248/518 |
| 3,116,046 A | 12/1963 | Risdon | 248/231.81 |
| 3,802,652 A | 4/1974 | Holton, Jr. | 248/534 |
| 4,821,988 A | * 4/1989 | Jimenez | 248/230.7 X |
| 4,877,165 A | 10/1989 | Behrle | 224/558 |
| 4,878,642 A | * 11/1989 | Kirby, Jr. | 248/230.1 X |
| 4,997,147 A | * 3/1991 | Velke, Sr. et al. | 248/230.7 |
| 5,356,107 A | * 10/1994 | Sinohuiz | 248/230.7 X |
| 5,407,161 A | * 4/1995 | Mulkeran | 248/231.81 X |
| 5,482,233 A | 1/1996 | Marko et al. | 248/73 |

* cited by examiner

Primary Examiner—Ramon O. Ramirez

(57) ABSTRACT

A system for holding small objects such as flashlights, containers of liquids for intravenous dispensing, tools, clamps, containers, receptacles, fishing rods, cooking utensils and the like. A bracket that attaches to an elongated prop such as an electrical conduit, pipe, railing, i.v. stand, wheel chair frame, stake, hospital bed guards, or post is disclosed. Bracket attachment is accomplished by placing the bracket perpendicularly over the prop and twisting the bracket ¼ turn. A variety of holders may be detachably attached to the bracket to enable a variety of objects to be held in a desired position. An interlocking, linked, positionable extension may be disposed between the bracket and the holder to enable the holder to be positioned as desired.

14 Claims, 6 Drawing Sheets

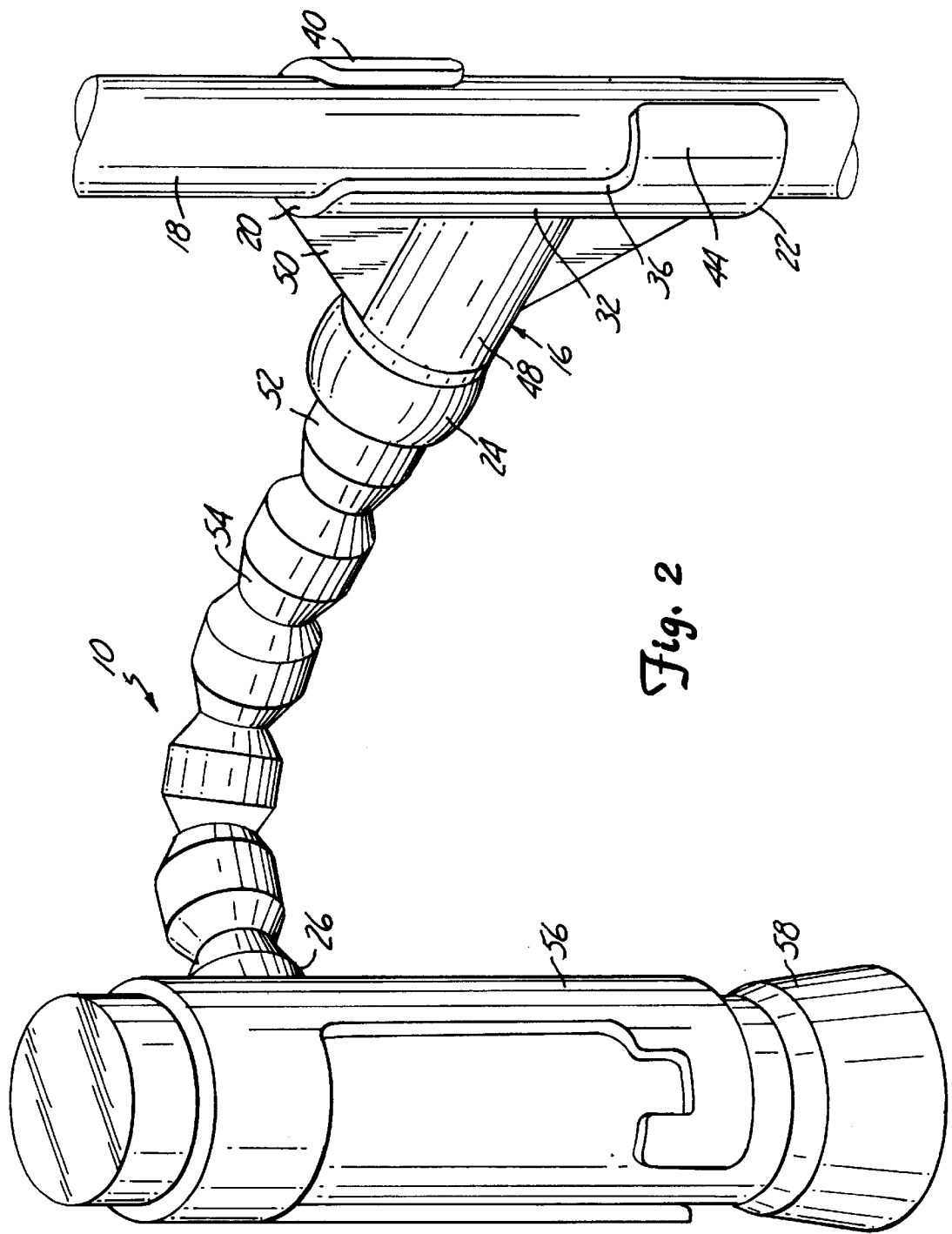

EASILY RE-POSITIONABLE, QUICK ATTACH AND REMOVE, MULTIPLE PURPOSE SUPPORT SYSTEM

TECHNICAL FIELD

The present disclosure relates to holders and supports, generally, and to multiple-purpose, light duty holders and support brackets that may be quickly mounted and de-mounted, in particular. Because the apparatus may be so readily installed and removed, it is particularly suited for supporting articles such as hospital bed controls, intravenous medication dispensers, blood bottles, telephones, beverage containers, flashlights, fishing poles, trays of small parts, w tools, or other objects that are preferably removed or relocated easily.

BACKGROUND AND SUMMARY

Many vocational and recreational activities are more easily performed if some object can be held in a desired position without the continuing assistance of a person. For example, it is often helpful to have a flashlight illuminate an object such as a threaded fastener or a knot while a person manipulates the object. Some tasks simply do not leave a person with a hand free to hold a needed tool or part.

To illustrate the generality of the problem, one need only consider the variety of techniques that have been tried to make light available at the location at which a person is working. Miners and campers have long used head lamps. A portable light can be mounted on a hat or headband and used to illuminate the area the wearer faces, but such head lamps can require frequent adjustment and often are quite annoying to other members of a group. One type of flashlight incorporates a magnet in the handle for holding it in place. Unfortunately, the orientation of an iron bearing surface is not always favorable for lighting purposes. Another flashlight has a clip for attachment to clothing, panels, or lines. Another type uses a heavy battery as a base and a pivotable lamp head to direct light to the desired area. None of these solutions has proven wholly satisfactory which suggests why so much inventive effort is directed to the field.

Building construction, repair, maintenance, equipment installation, machine work, vehicle repair and maintenance, and home projects are among the activities that often must be undertaken in substandard lighting conditions. Workers in these activities often must carry all of the tools that they expect to use for a specific job long distances to reach the location at which the work will be performed. It is rarely practical to carry bulky or complex additional items such as light stands in addition to the tools, parts and materials that are required. Workers will frequently carry flashlights to enable them to go forward with their appointed tasks. They might carry and use simple, lightweight, compact mounting brackets to allow them to use their flashlights to illuminate a work area more easily if such brackets were known to work.

Hospitals are an example of an environment in which specialized arrangements of tubes, containers, wires, sensors, controls, and other items must be established temporarily, for periods ranging from a few minutes to several days. Although hospitals use rails to restrain patients from accidentally sliding out of bed, patients often find that things like call buttons, operating controls, and telephones do slide out of their reach. If easily attached and easily removed support brackets for holding items in the desired arrangement around patients could be provided at low cost, hospitals might find fewer requests for nursing assistance to re-locate television or bed operating controls that slip beyond a patient's reach.

Another example of an environment in which it is often difficult for people to properly secure needed items is the wheel chair. Persons who rely on wheel chairs or motorized chairs for their mobility often find it difficult to keep often used items such as a drinking vessel, a notepad, a urine collection bag, or other personal items secured and accessible within the confines of the wheel chair structure. The present disclosure gives wheel chair users a simple means for conveniently securing the previously mentioned articles, as well as many others, to the chair.

People who fish from the banks of lakes, rivers or ponds often find it inconvenient to hold their fishing poles or rods continuously. Ingenious fishing rod holders have been proposed; U.S. Pat. No. 1,410,798 to Cowdery is but one example. However, the previously patented fishing rod holders suffer from one or more shortcomings: the mechanism may be too complex, the range of adjustment too small, the apparatus too cumbersome, or the mounting requirements impractical to fulfill.

Of course, temporary lighting for people in the construction trades, temporary hospital patient fixtures and accessory retainers, and temporary holders for fishing rods are but examples that illustrate representative uses for temporary holders and supports. Many other activities are made easier if temporary supports or holders can be readily set up and removed with a minimum investment of time and expense.

My discovery solves many of the problems inherent in previously known temporary supports. It is easy to install, inexpensive, simple, lightweight and compact. One embodiment I disclose can be attached to an existing building structural component (e.g. ½ inch electrical conduit) by placing the bracket portion over the structural component and twisting the bracket ¼ turn. Likewise, the present apparatus can be mounted to a great variety of fixed elongated members with a simple ¼ turn. For example, the bracket may be attached to safety rails, ring stands, hospital bedposts, electrical conduit, water pipes, gas pipes, scaffolding, and many other solidly mounted structural elements such as brackets, mounts, standards, holders, and the like. For ease of reference, the object to which my bracket attaches will be called a prop, and the term prop is explicitly defined to include all objects to which my bracket can be attached. It is possible to use the handles of a two-wheeled hand truck as props. It is likewise possible to use the handle of a cart, or of a broom, as the prop to which an embodiment of the present multiple-purpose support system attaches.

After the bracket is attached to a prop, the bracket may be used to support any desired object that weighs less than the holding capacity of both the bracket and of the prop, as configured. In one embodiment, the bracket is fitted with a hook from which a blood bottle can be suspended. In another embodiment, the bracket is fitted with a series of hooks capable of holding several objects, for example, frequently used tools. In another embodiment, the bracket may be fitted with a spring clamp that can hold objects such as a map, a set of instructions, a sign, or the like. In another embodiment, the bracket may be fitted with one end of a bendable, non-resilient, shape-retaining linkage that has a holder at its other end. One example of such a linkage is the snap-apart flexible coolant conduit manufactured by Lockwood Industries of Lake Oswego, Oregon.

Although many other utility support devices and brackets have been designed, one problem remains that none has successfully overcome—the necessity of compromising the design of the device so that it is sufficiently rigid to support the desired object from the lever arm created by the device itself, without making the device excessively rigid, heavy, bulky or wasteful of materials. It is to be appreciated that any support member will perform more satisfactorily if the purpose to which it is put is appropriate for the design. This principle can be illustrated by consideration of the ordinary laboratory ring stand.

A laboratory ring stand usually has as its base a fairly heavy rectangular plate that is placed flat on a laboratory bench. Securely attached toward one end of, and perpendicular to, the upper surface of the plate is a rod that extends upward about two feet. A clamp can attach a second rod perpendicular to the vertical rod so that the second rod extends parallel to the laboratory bench.

It is to be understood that when a load applied to the second rod is situated farther from the vertical rod, the lever arm is effectively increased. The longer lever arm applies more torque to the clamp. When the load exceeds the capacity of the components, the arrangement will tip, bend or break. If the clamp is made stronger, the clamp will not break, but some other component of the system will either bend or tip. The difficulty in designing the proper clamp strength is that the length of the lever arm can vary, as can the load.

One embodiment of my system provides improved performance because the torque load that can be transferred to the bracket is fixed. By using a bendable, non-resilient, shape-retaining, linkage between the bracket and the object being held, the system is prevented from overloading. When the load exceeds the torque capacity of the linkage, it will simply deflect so as to prevent overloading that would damage components of the support system.

To better illustrate this benefit of my system, it may be useful to compare what might happen if someone were to temporarily support a light from an installed section of rigid pipe. A clamp might be attached to the pipe by tightening a screw. A horizontal member may be attached to the pipe and a light suspended from it. If the horizontal member is lengthened and a second light added, the rigid pipe might then be so loaded that the fasteners holding it in place would give way. Using my system, however, the interlocking conduit would simply bend as soon as the load exceeded the holding power of any of the individual interlocking sections.

In addition to the first advantage of my system, that it can be installed and removed quickly and easily; and the second advantage, that it is less likely to be accidentally overloaded; a third advantage of my system, compared to the support systems previously known, is that it is readily adaptable for fitting to a variety of previously installed props in addition to being suited for ready mounting on receiving apparatus fabricated expressly for the bracket disclosed herein. A small assortment of brackets of the type disclosed in the accompanying figures can be adapted for attachment to a wide range of pipes, rods, tubes, bars, and structural shapes. It is also possible to incorporate bushings or adaptors that allow the present system to connect to an extended size range of props.

Although the bracket of the present system may be made of a variety of materials, such as steel, spring steel, and several polymers, it is known that one material that can be used is injection-molded polyvinyl chloride. It is also possible to fabricate the bracket using coated or composite materials. Likewise, it is known that the interlocking conduit from which the positionable extension portion is preferably made can be manufactured from a variety of materials, preferably polymeric materials. Additional elements, such as hooks, clasps, hangers, trays and other holders that are connected to the bracket portion directly or by means of interlocking conduit may be made of any of a number of materials, including wood, metal and plastic, found suitable for a particular application.

It is to be understood that a particular advantage of the present bracket is that it is believed that the cost to manufacture it is low enough that it will be possible to use it as a single-use item. This low cost of manufacture and high versatility make the bracket particularly adapted for use in hospital, clinical and other medical settings.

There have been attempts to fashion supports that are easily installed and removed. For example, U.S. Pat. No. 1,105,083 to Lamb discloses an electric light support made of thin leaf springs that are brought into proximity with the member to which the support is attached with the potential for marring the surface during use. Behrle in U.S. Pat. No. 4,877,165 discloses a fishing rod holder into which a rod may be quickly fitted and from which the rod may be easily removed. However, neither device is adapted for general purpose holding applications. The attempts others have made to develop a general purpose holder that can take advantage of existing structural features to support objects have not been successful. Earlier attempts have generally failed either because the apparatus was insufficiently versatile or because the mounting requirements were too difficult for the user to fulfill.

DISCLOSURE OF THE INVENTION

What is needed, then, is a support system that may be easily attached to a variety of commonly found support structures such as hospital bed frames, wheel chairs, laboratory stands, electrical conduits, water pipes, structural tubing, and the like. In addition, the support system must be easy and quick to install and remove without tools. This support system may, for example, be used to hold intravenous bottles to a support rod or to an i.v. stand in a clinic or hospital. A preferred embodiment of the invention is adapted to attach to the safety rails commonly used with hospital beds. It may also be attached to an installed length of pipe, electrical conduit, railing, or other support structure to hold objects such as a tray of parts, a work light, a fishing pole, or other items.

The present invention is easily installed by placing the open side over a prop and then twisting the bracket ¼ turn to engage it fully with the prop. A slightly different embodiment is preferred for brackets that mount on props that have a square cross-section than is believed optimum for brackets that are used on props that have a round cross-section.

The preferred embodiment includes an elongated central member, or saddle, and two oppositely facing "C" shaped resilient members, or arms, one at each end of the central member, the arms and saddle having a common longitudinal axis. In an embodiment adapted for attachment to support members that have square cross-sections, the arms are "L" shaped rather than "C" shaped and the saddle may be angled rather than curved. An attachment element, or adaptor barrel, extends generally radially outwardly from the central member and is generally perpendicularly to the longitudinal axis. It is also possible to provide gussets or wings that extend outward from the central member so that the bracket may be more easily manipulated and to strengthen the bracket.

The attachment element may be a specific element such as a hook, a clamp, or a specialty holder. More generally, the attachment element may be a shape adapted for receiving a positionable extension portion, preferably a non-resilient, flexible, interlocking conduit-type elongated linkage. In some embodiments, it may be preferred to use electrically conductive materials or coatings to reduce static electricity build-up and/or to provide power or signal transmission. The interlocking linkage may connect to the bracket at one end and have connected to the other end any of the holders, clamps, hooks, bags, lights, trays, or other devices that may be desired by the user.

BRIEF DESCRIPTION OF THE DRAWING

FIG. 2 is a perspective view of the embodiment of FIG. 1 fitted to a prop that has a circular cross-section and wherein the hook is replaced with non-resilient interlocking conduit that is terminated with a flashlight holder.

FIG. 1 A is a plan view of the embodiment of FIG. 1.

DETAILED DESCRIPTION OF THE DRAWING

Figure 1:
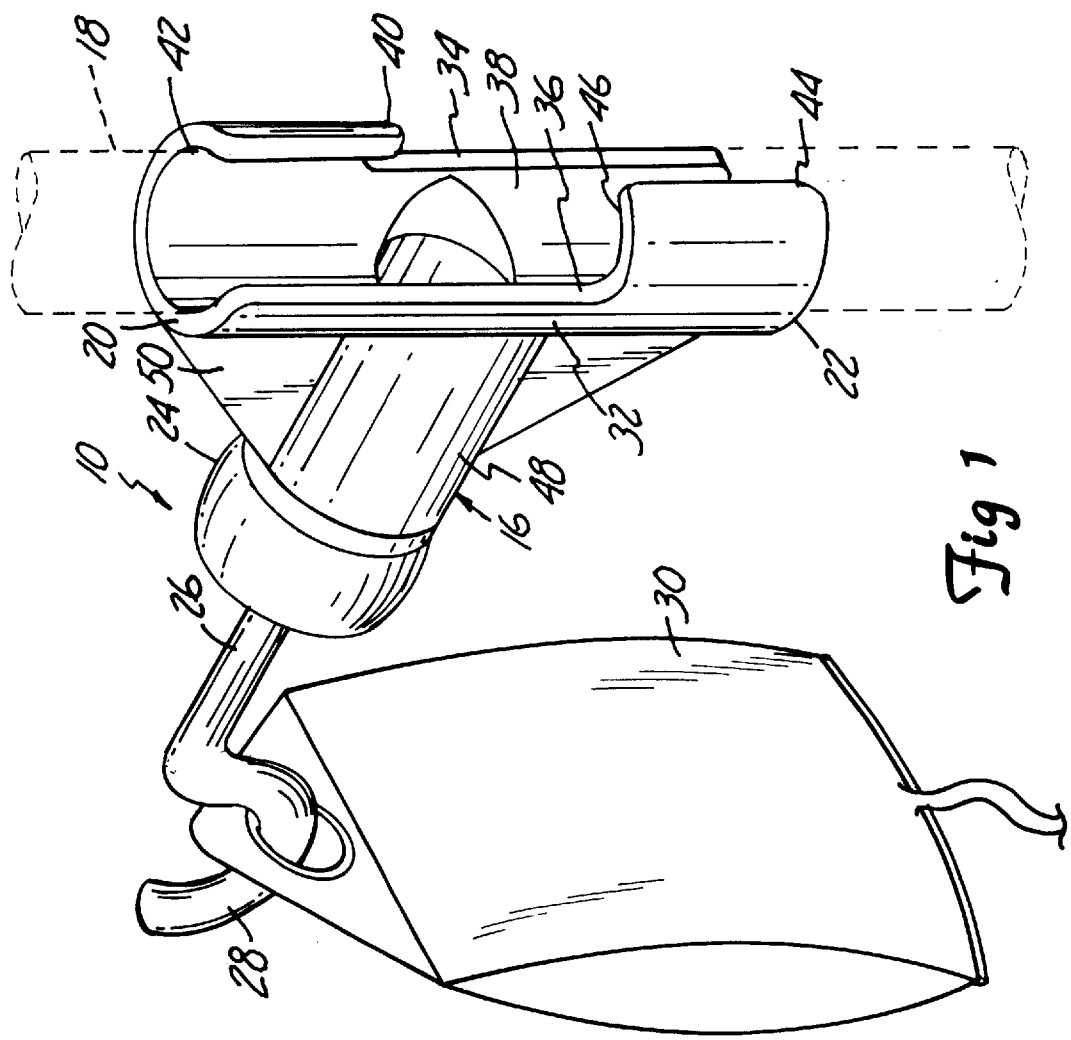
FIG. 1 is a perspective view of an embodiment of the invention equipped with a hook for holding objects such as blood bags.

Referring to FIG. 1, a support system 10 is shown that includes a bracket 16 that can connect to a prop 18 of any sort, such as a hospital bed rail, a length of electrical metallic tubing, an intravenous stand, or the like which is shown in outline. The prop 18 is shown in FIG. 1 through FIG. 4 as having a round cross-section. In FIG. 5, the prop 18 is shown as having a square cross-section. To simplify the description, it is to be understood that the cross-section of the prop 18 and the specific adaptations of any embodiment to be fitted to such a prop 18 having a particular cross-section shall not be construed to limit the scope of this disclosure and the teachings set forth, herein.

The bracket 16 preferably has a first end 20, a second end 22 and an adaptor 24 that extends outwardly, away from the prop 18. The adapter portion 24 can matingly connect to any of a selection of attachable and detachable holders 26 including, among others, a hook 28 of the type used in hospitals to hold blood bags 30.

The bracket 16 includes a saddle 32 that is, when mounted, oriented on the same axis as the prop 18 and is shaped so that, when mounted, it matingly contacts the periphery of the prop 18. The saddle 32 has a first side 34 and a second side 36. The saddle portion 32 of the bracket 16 has a saddle inner surface 38. A first resilient arm 40 extends from the first end of the saddle 32. The saddle inner surface 38 is contiguous with the first arm inner surface 42. A second resilient arm 44 having a second arm inner surface 46 that is contiguous with said saddle portion inner surface 38 extends from the second end of the saddle portion 32 that is opposite the first resilient arm 40.

The resilient arms 40, 44 are configured so that when the bracket 16 is not attached to a prop 18, the arms 40, 44 can be deflected from their relaxed state to attach the bracket 16 to a prop 18. It is the springiness or resilience of the arms 40, 44 that allows a person to attach and detach the bracket 16 quickly and easily. The correct degrees of rigidity and of resilience make it possible to fabricate a bracket 16 that can grip or otherwise claspably engage a wide size range of props 18 and also be sufficiently strong to be functional. Regardless of the shape of the prop 18, the first arm 40 is shaped to extend from the first side 34 of the saddle 32 to cover a portion of the periphery, or outer surface, of the prop 18. The second resilient arm 44 extends from the second side 36 of the saddle 32, in the opposite direction from the direction in which the first arm 40 extends, to cover an additional portion of the periphery of the prop 18. The resilient property of the arms 40 44 causes them to grip, clasp, bind, engage or otherwise secure the saddle 32 to the prop 18.

Extending radially from the saddle 32 is a barrel portion 48 which may be solid or hollow and of any convenient cross-section, although it is believed that a circular cross-section of the barrel 48 is preferable. The adaptor 24 may be so shaped that it integrates the function of the barrel 48 which is to provide a structure that connects the saddle 32 to any utensil detachable holder 26 or linkage desired. A generally longitudinal, generally planar graspable surface such as the preferred gussets 50 may optionally be used to reinforce the connection of the barrel 48 to the saddle 32. It is to be appreciated that the gussets 50 could also serve as features that may be grasped during installation of the bracket 16 onto a prop 18 and the subsequent removal of the bracket 16. It is to be understood that the gussets 50 are optional and that other graspable portion may be included instead to make installation and removal of the bracket 16 easier.

FIG. 2 shows the bracket 16 of the support system 10 fitted onto a cylindrical prop 18. The holder 26 depicted includes positionable extension 52 portion that may be made of any convenient material, including lead shapes, coil materials, frictional moveable hinges, ball and socket fittings, gimbals, and the like, but is preferably comprised of an interlocking linked material 54 fitted to the adaptor 24. The interlocking linked material 54 can be made of a wide variety of materials. A preferred type of interlocking linked material 54 is a plastic conduit such as the ¾" coolant conduit made by Lockwood Industries of Lake Oswego, Oregon for carrying machine and work piece coolants, among other things.

It is possible to fit a holder 56 for holding a flashlight 58 to the distal end of the interlocking linked material 54. The flashlight holder 56 illustrated is representative of all the holders that might be attached to the interlocking linked material 54 for holding objects.

Figure 3:
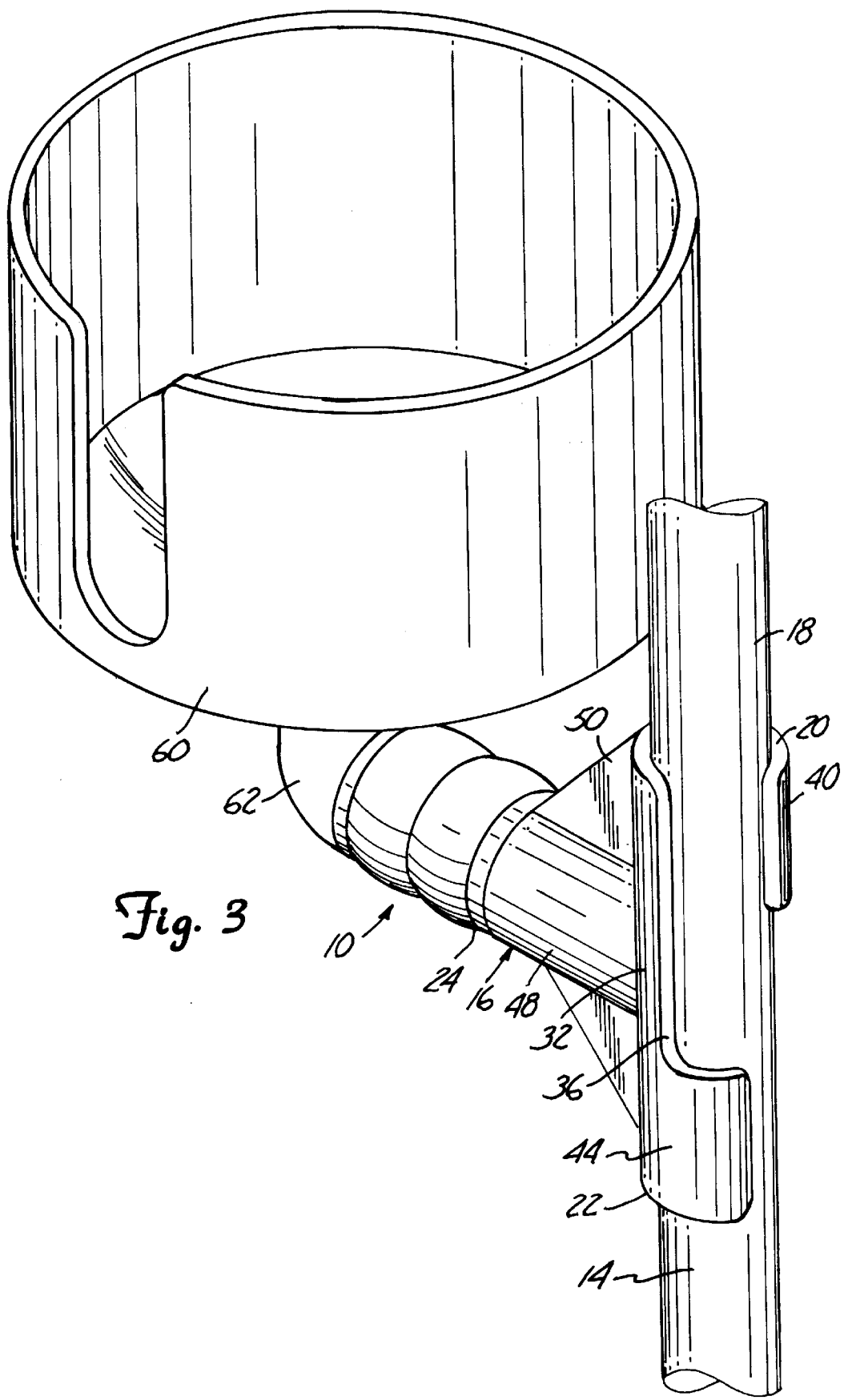
FIG 3 is a perspective view of the embodiment of FIG. 1 wherein the hook is replaced with a holder suitable for holding beverage containers.

FIG. 3 discloses a bracket 16 attached to a prop 18. A short length of interlocking linked material 54 communicates between the bracket 16 and a holder for holding containers 60 such as cups or bottles. It is to be understood that a cupholder 60 can be configured in many other arrangements without departing from my invention.

It is possible to fit the interlocking linked material with angled adaptors and terminators. A 90° elbow adaptor 62 is shown for ease in adapting the cupholder 60 for attachment to the prop 18.

Figure 4:
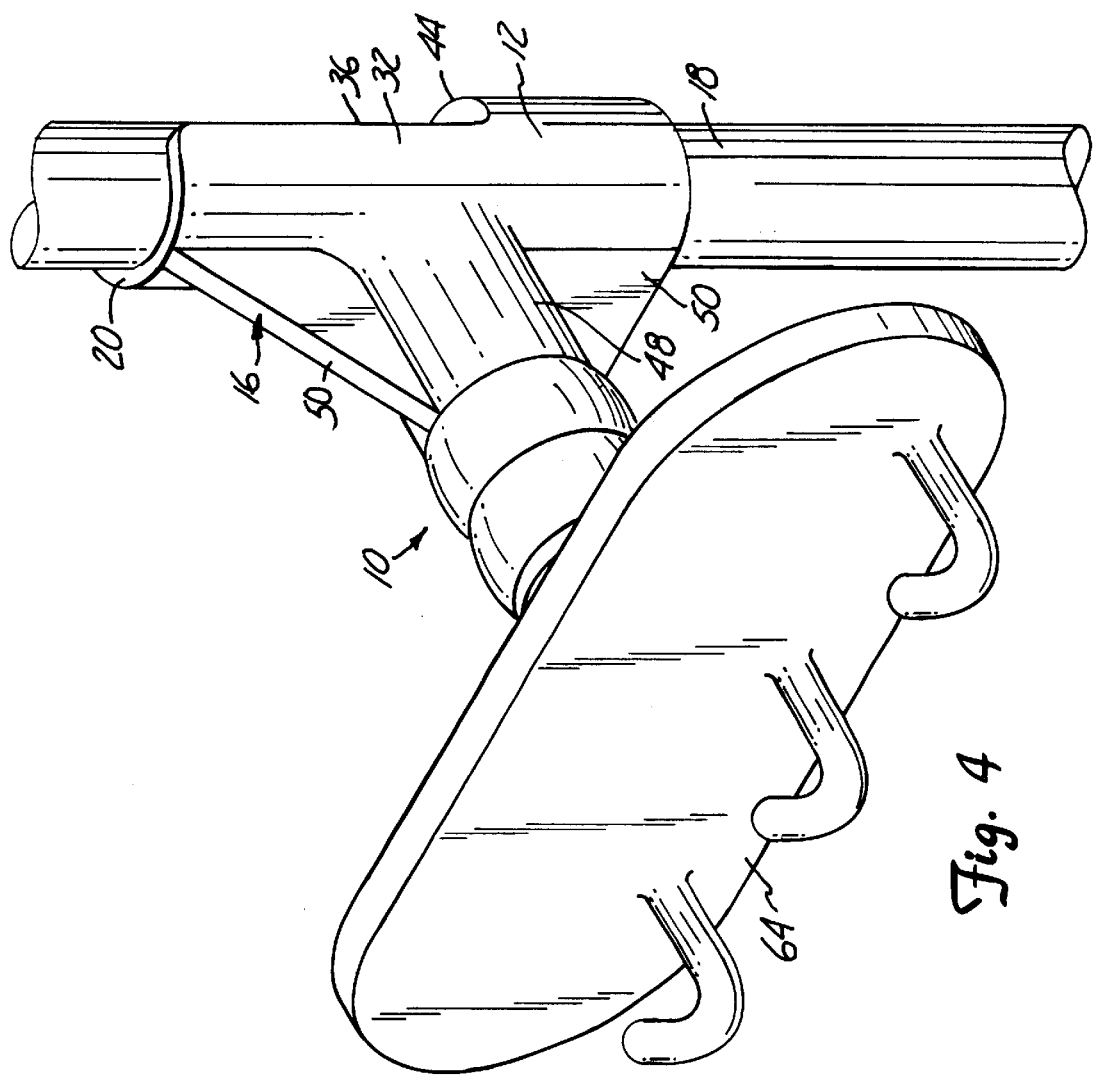
FIG. 4 is a perspective view of the embodiment of FIG. 1 wherein the single hook is replaced by a holder that includes multiple hooks.

FIG. 4 shows another view of the bracket 16. Another type of holder, a multiple hooked hanger 64 that may be used for holding tools, cookware, and other utensils is shown linked to the bracket 16. It is anticipated that a multiple hooked hanger 64 will be useful to persons who, while camping need to keep cooking utensils, skillets, pots, pans, and other items within reach and suspended above the ground. The holder 64 can also be used by persons who are fishing.

It is most readily seen in FIG. 4 that the gussets 50 not only reinforce the attachment of the barrel 48 to the saddle 32 but also act as wings for grasping when attaching and removing the bracket 16 from a prop 18.

In a preferred embodiment, the bracket 16 is constructed to fit a prop 18 that is 11/16" diameter. That diameter is commonly used in industrial construction. However, it is to be recognized that the bracket 16 can be made to fit a prop 18 of any desired diameter.

When viewing FIG. 4, it may be seen that in order to remove the bracket 16 from the prop 18, it would be necessary to rotate the barrel and saddle counterclockwise to move the arms 40, 44 out of contact with the prop 18. It may be seen that the arms 40, 44 will necessarily deflect to allow the prop 18 to pass through the gap between the ends of the arms 40, 44 and the saddle 32. When the bracket 16 has been rotated ¼ turn counter-clockwise, the prop will be between the first arm 40 and the second arm 44, and the longitudinal axis of the saddle 32 perpendicular to the longitudinal axis of the prop 18. The bracket 16, being disconnected from the prop 18, may be withdrawn. The bracket 16 is attached to the prop 18 by reversing the procedure for removing the bracket 16 from the prop 18.

It will be appreciated that it may be necessary to provide gussets 50 or some other readily gripable surface to enable people to remove the bracket 16 without using tools.

The bracket 16 may be made from cpvc or polyvinyl chloride or any other polymer or metal having the necessary properties of resilience and rigidity. When cpvc is used, the arms 40, 44 have both sufficient flexibility to be attach to, and removed from, a prop 18 easily while also having sufficient rigidity to grip a prop 18.

It is preferred to relieve the edges and corners of the components described, as is illustrated. Although it may not be necessary to round the corners and edges of the components, it is preferred to reduce the incidence of scratches and breakage and also to make the components easier to use.

FIG. 5 depicts an embodiment wherein the bracket 16 that is shaped so that it is adapted for attachment to a prop 18 that has a square or rectangular cross-section. In this alternative embodiment, the gussets 50 and barrel 48 extend from the apex of a V-shaped saddle 32. In an embodiment adapted for attachment to a square cross-sectioned prop, the arms 40 and 40 would be angled, or L-shaped, rather than generally arcuately curved, or C-shaped as they would be when adapted for attachment to a prop having a circular cross-section. Although not explicitly depicted in the drawing, it is to be understood that the arms may also be extended at conforming angles to cover, grip or mate with, additional sides, or faces, of a polygonal prop 18 without departing from this disclosure.

Although FIG. 5 shows arm 40 and arm 44 as having the same length. It is to be understood that embodiments that have arms 40 and 44 of different lengths will be useful for attaching to some rectangular shapes. It is further to be understood that the dimensions and shapes of the embodiment and of the components of the embodiment are variable and may be adapted to suit the purposes for which this support system is intended. The saddle 32 and arms 40, 44 may be formed in any appropriate shape, to attach to a prop 18 including props 18 having cross-sections that are circular, square, rectangular, and other curved and polygonal shapes.

It is to be understood that the cross-sectional shape of the saddle 32 and arms 40, 44, of a bracket 16 adapted for attachment to a prop 18 having a circular cross-section such as a round rod, when viewed from the longitudinal axis of the saddle 32, would be curved. The curvature of the saddle 32 and arms 40, 44 of such a bracket 16 would be generally, but not necessarily exactly, circular when the bracket is not attached to a prop 18 and, when the bracket 16 is attached to a prop 18, the curvature would tend to conform to the cross-sectional shape of the prop.

A lip 66 may terminate the arms 40, 44 regardless of whether the bracket 16 is configured for attachment to square, other polygons, or circular cross-sectioned props 18.

It is to be understood that the barrel 48 may be either hollow or solid.

Figure 1A:
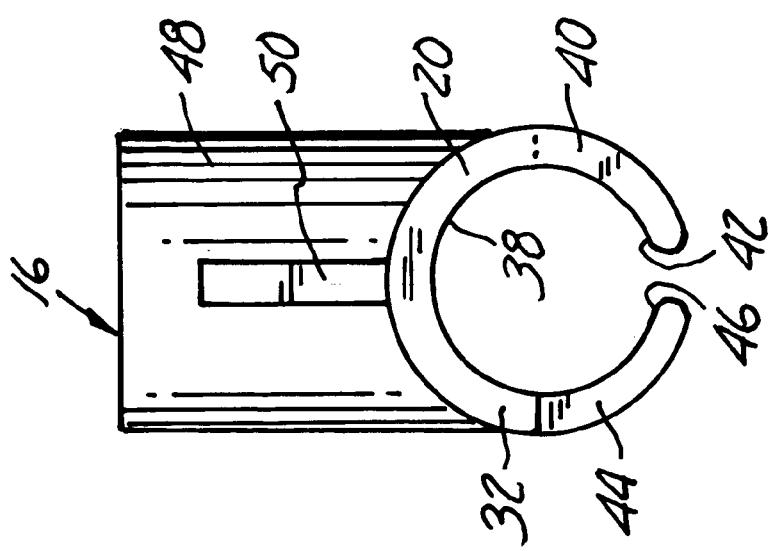

FIG. 1A is a plan view of the embodiment of the bracket shown in FIG. 1 showing in greater detail one preferred shape for the saddle 32, first arm 40 and second arm 44.

Figure 5A:
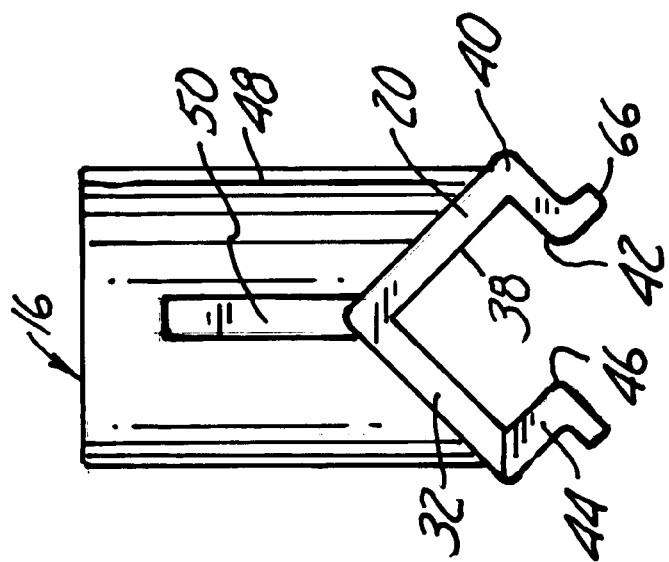
FIG. 5A is a plan view of the embodiment depicted in FIG. 5.
Figure 5:
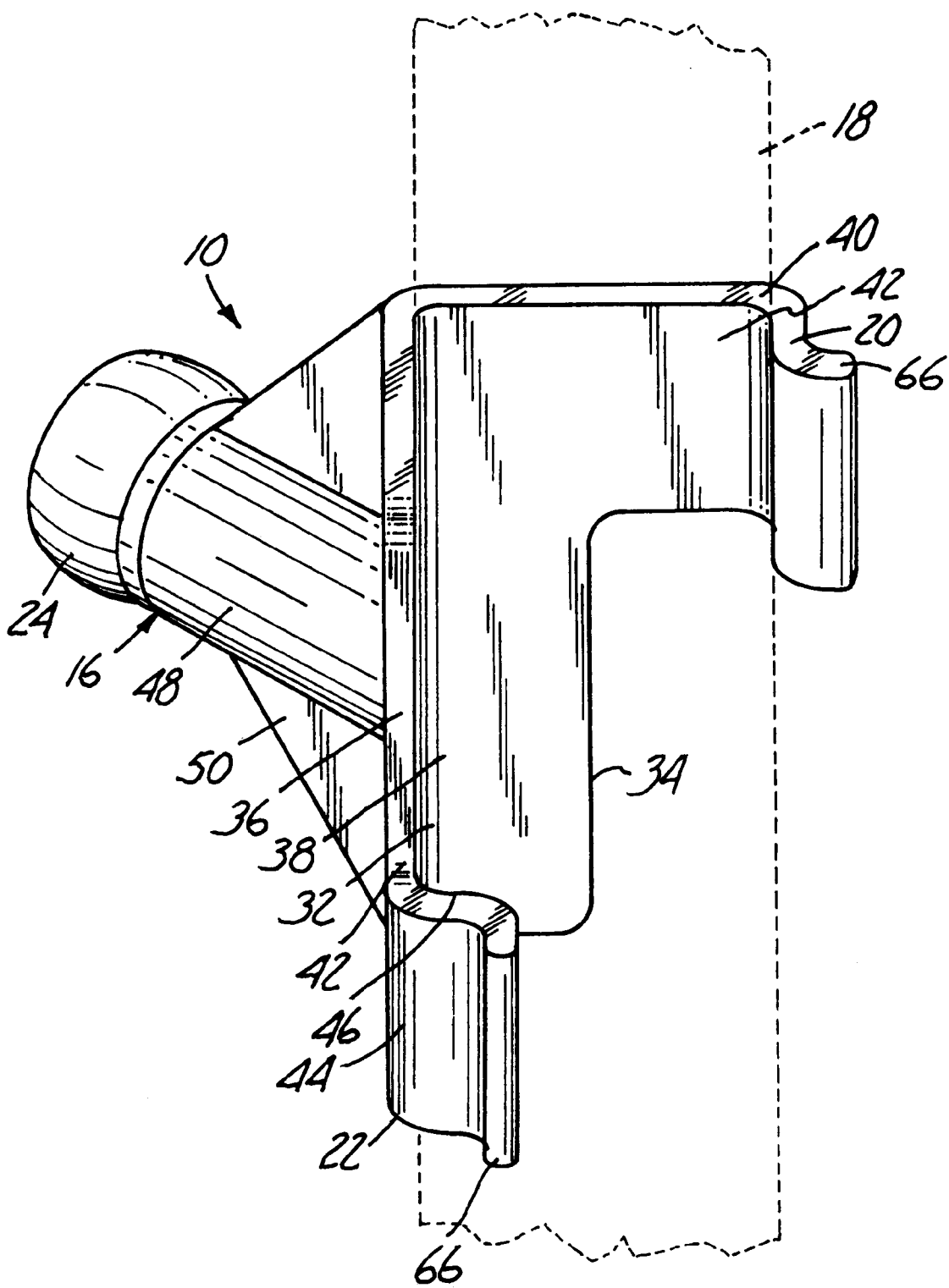
FIG. 5 is a perspective view of the embodiment of FIG. 1 that is adapted for fitting to a square prop.

FIG. 5A is a plan view of the embodiment of the bracket shown in FIG. 5 showing in greater detail a second preferred shape for the saddle 32, first arm 40 and second arm 44.

Changes and modifications in the specifically described embodiments can be carried out without departing from the scope of the invention which is intended to be limited only by the scope of the appended claims.

DRAWING REFERENCE NUMBERS 10 support system
16 bracket
18 prop
20 bracket first end
22 bracket second end
24 adaptor
26 detachable holder
28 hook
30 blood bag
32 saddle portion
34 first saddle side
36 second saddle side
38 saddle inner surface
40 first arm
42 first arm inner surface
44 second arm
46 second arm inner surface
48 barrel
50 gusset
52 positionable extension
54 interlocking linked material
56 flashlight holder
58 flashlight
60 container holder
62 90° elbow
64 multiple hooked hanger
66 lip

I claim:

1. A support system twistably attachable to an elongated prop comprising:
   a bracket having an elongated saddle adapted to matingly fit the outer surface of the elongated prop, said elongated saddle having;
      an outer surface,
      an inner surface shaped to be matingly disposable against the outer surface of the elongated prop,
      a first side,
      a second side,
      a first end,
      a first resilient arm situated at said first end and extending from said first side claspably peripherally partially around said prop, a second end, a second resilient arm situated at said second end and extending from said second side opposite said first resilient arm, claspably peripherally partially around said prop, an adaptor extending from said outer surface of said elongated saddle, said adaptor being shaped to matingly attach a detachable holder, and a pair of generally planar, generally longitudinal graspable surfaces extending radially between said bracket and said saddle outer surface.

2. The support system as defined in claim 1 wherein each of said resilient arms has an inner surface generally continuous with the inner surface of said elongated saddle.

3. The support system as defined in claim 2 wherein the shape described by said inner surface of said bracket has a cross-section that is generally arcuately curved.

4. The support system as defined in claim 2 wherein the shape described by said inner surface of said bracket has a cross-section that is generally rectangular.

5. The support system as defined in claim 4 wherein the shape described by said inner surface of said bracket has a cross-section that is generally square.

6. The support system as defined in claim 6 wherein the bracket has generally planar, generally longitudinal graspable surfaces extending outwardly from said saddle portion.

7. The support system as defined in claim 6 wherein the detachable holder is further comprised of a holding portion and a positionable extension portion, said positionable extension portion being comprised of interlocking linked material.

8. The support system as defined in claim 7 wherein the holding portion is comprised of a hook.

9. The support system as defined in claim 7 wherein the holding portion is comprised of a clip.

10. The support system as defined in claim 7 wherein the holding portion is comprised of a receptacle.

11. The support system as defined in claim 10 wherein the bracket has generally planar, generally longitudinal graspable surfaces extending outwardly from said saddle portion.

12. The support system as defined in claim 11 wherein the holding portion is comprised of a plurality of hooks.

13. The support system as defined in claim 11 wherein the holding portion is comprised of a flashlight holder.

14. The support system as defined in claim 11 wherein the holding portion is comprised of a receptacle.

* * * * *